US007300418B2

(12) United States Patent
Zaleski (10) Patent No.: US 7,300,418 B2
(45) Date of Patent: Nov. 27, 2007

(54) HEALTHCARE SYSTEM SUPPORTING MULTIPLE NETWORK CONNECTED FLUID ADMINISTRATION PUMPS

(75) Inventor: John R. Zaleski, West Brandywine, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 526 days.

(21) Appl. No.: 10/645,234

(22) Filed: Aug. 21, 2003

(65) Prior Publication Data

US 2004/0181314 A1    Sep. 16, 2004

Related U.S. Application Data

(60) Provisional application No. 60/453,320, filed on Mar. 10, 2003.

(51) Int. Cl.
*A61M 37/00* (2006.01)
(52) U.S. Cl. .................... 604/131; 604/19; 604/65; 604/151; 741/8
(58) Field of Classification Search ............. 604/65, 604/131, 151; 710/8
See application file for complete search history.

(56) References Cited

U.S. PATENT DOCUMENTS 5,041,086 A   8/1991  Koenig et al. ............... 604/65
5,590,648 A   1/1997  Mitchell et al.
5,681,285 A  10/1997  Ford et al. ................ 604/151
5,772,635 A   6/1998  Dastur et al. .............. 604/131
5,857,194 A   1/1999  Kelliher et al.
5,924,074 A   7/1999  Evans
5,935,099 A   8/1999  Peterson et al. ............. 604/65
6,241,704 B1  6/2001  Peterson et al. ............. 604/65
6,475,180 B2 11/2002  Peterson et al. ............. 604/65
2001/0031944 A1 10/2001 Peterson et al.
2002/0038392 A1* 3/2002 De La Huerga ............. 710/8
2002/0077852 A1  6/2002 Ford et al. ..................... 705/2
2002/0126036 A1  9/2002 Flaherty et al. ............ 341/176
2002/0183693 A1 12/2002 Peterson et al. ........... 604/151

\* cited by examiner

*Primary Examiner*—Kevin C. Sirmons
*Assistant Examiner*—Phillip Gray
(74) *Attorney, Agent, or Firm*—Alexander J. Burke (57) ABSTRACT

A system and user interface according to invention principles supports concurrently managing and maintaining multiple medical devices (e.g., infusion pumps) and processing and displaying the data produced by the medical devices within a Healthcare enterprise. An information system supports a plurality of network connected infusion pumps. The system includes an acquisition processor for acquiring fluid infusion related data from a plurality of concurrently operating infusion pumps. A data processor processes the acquired fluid infusion related data to provide data suitable for presentation in a single display image identifying the plurality of concurrently operating infusion pumps together with status information identifying status of individual pumps of the plurality of concurrently operating infusion pumps.

16 Claims, 7 Drawing Sheets

IV Pump Manager

Username [         ]

Password [         ]

IV Pump Manager

Username [ Zaleski           ]

Password [ *********** ]

| IV Pump ID | Location | State | Access Point MAC Address | Pump Up-Time (HH:MM:SS) |
|---|---|---|---|---|
| 1006 | 3 West | Run | 00:09:CD:43:6F:3C | 03:25:08 |
| 1022 | 5 North | Hold | 01:18:FE:56:8B:2A | 00:35:40 |

405 → Refresh Now

HEALTHCARE SYSTEM SUPPORTING MULTIPLE NETWORK CONNECTED FLUID ADMINISTRATION PUMPS

This is a non-provisional application of provisional application serial No. 60/453,320 by J. R. Zaleski filed Mar. 10, 2003.

FIELD OF THE INVENTION

This invention is related to an information system supporting a plurality of network connected medical devices such as infusion pumps.

BACKGROUND OF THE INVENTION

Hospitals and other healthcare delivery settings employ different medical devices in treating patients. These medical devices include patient monitoring equipment for acquiring patient medical parameter data, breathing support equipment, anesthesiology equipment and fluid intra-venous (IV) infusion pumps, for example. Such medical devices are usually located at a patient bedside or nursing station in a hospital ward or in an intensive care, surgical or other location. Further, the medical devices may be connected by a wired or wireless connection to a network such as the Internet, a LAN, a WAN or an intra-net for acquiring patient parameter data and monitoring and controlling the devices. Patient medical parameter data acquired from such devices may include vital signs, ventilator information, infusion pump data associated with fluid delivery and other data.

Known infusion pumps feed information to a recipient data manager that stores raw infusion pump data in a file (e.g., in a flat file format) that is continually updated. The data that is arriving from the infusion pumps is used by medication administration systems to assist in monitoring and managing patient care. However, while this information may be formatted and sent to these systems on an individual basis, existing pump and medication administration systems fail to support the management of the operation of multiple pumps operating concurrently within a healthcare enterprise. A system according to invention principles addresses these limitations and derivative problems.

SUMMARY OF THE INVENTION

A system according to invention principles supports concurrently managing and maintaining multiple medical devices (e.g., infusion pumps) and processing and displaying data associated with or produced by the medical devices within a Healthcare enterprise. An information system supports a plurality of network connected infusion pumps. The system includes an acquisition processor for acquiring fluid infusion related data from a plurality of concurrently operating infusion pumps. A data processor processes the acquired fluid infusion related data to provide data suitable for presentation in a single display image identifying the plurality of concurrently operating infusion pumps together with status information identifying status of individual pumps of the plurality of concurrently operating infusion pumps.

DETAILED DESCRIPTION OF INVENTION

A system according to invention principles supports concurrently managing and maintaining multiple infusion pumps (or other medical devices) and processing and displaying the data associated with or produced by the multiple infusion pumps in a single composite user interface image. The system advantageously assists in patient care management, medication administration and pharmacy management, and in maintaining an electronic patient record (EPR). In addition, the system includes a database manager and user interface supporting user review of substantially real-time and non-real-time data associated with multiple infusion pumps. The data is accessible by authorized personnel via a web browser executing on a Microsoft Windows compatible PC, for example, within a hospital, or remotely via a LAN (Local Area Network) network. A Web compatible viewer application enables display of data related to multiple infusion pumps operating continuously on a network and enables viewing of the data using a workstation with a Web browser from within or via a virtual Private Network (VPN) in a Healthcare enterprise, for example. The Web compatible viewer application supports access to infusion pump data of multiple patients via different communication interfaces including a Health Level 7 (HL7) interface. Such access supports patient monitoring results reporting as well as patient Admission Discharge and Transfer management. The viewer application enables a user to send validated infusion pump and other patient data to a recipient application in Health Level 7 (HL7) compatible format.

Figure 1:
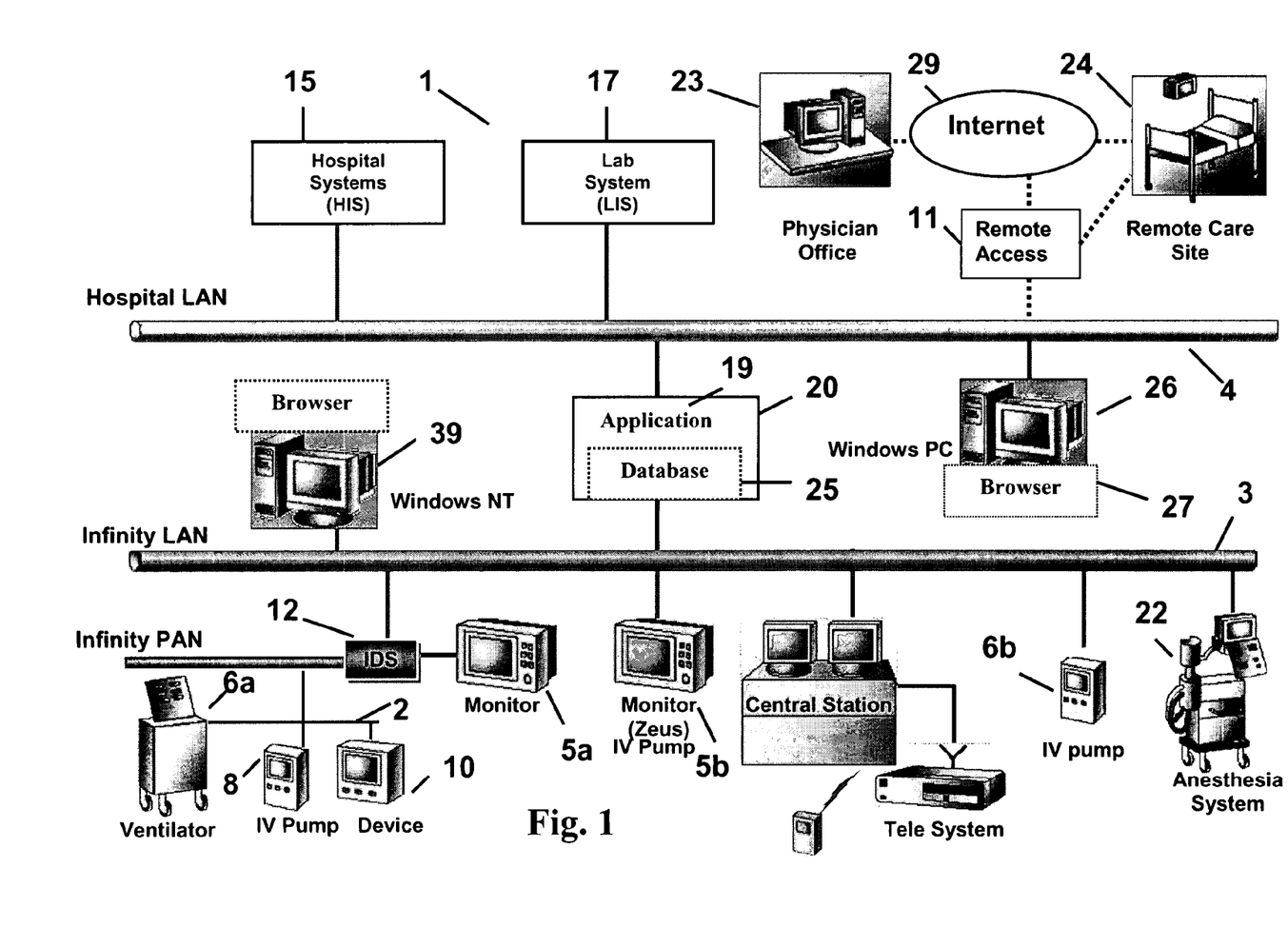
FIG. 1 is a block diagram of a communication network with various devices and multiple infusion pumps, according to the principles of the invention.

FIG. 1 is a block diagram of a communication network with various devices and multiple infusion pumps. The communication network incorporates server 20 hosting executable Web compatible viewer application 19 supporting access to infusion pump data of multiple patients via different communication interfaces according to invention principles. Executable application 19 in other embodiments may be resident in another processing device in any part of the network shown in FIG. 1. Communication Network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown In FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a care unit such as a patient's room within a nursing station to administer care to a particular patient and to monitor the particular patient. Various medical devices may be connected via MIB 2; examples shown in FIG. 1 comprise a ventilator 6a, a first infusion Pump 8 or other medical equipment 10. MIB 2 is typically connected to a second level LAN network 3 through an Interface Docking Station (IDS) device 12, for interfacing to Ethernet-compatible LAN network 3. This higher-level LAN 3 is typically, though not necessarily, used by other care units such as a particular department within a hospital, for instance an intensive care unit or surgery unit, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a second infusion pump 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory system (LIS) 17. In addition, the Hospital LAN 4 has a remote access gateway 11 which provides remote, secured access to information from, for example, a remote doctor's office 23 or a remote care site 24, to the various systems and devices on network 1, through for example, Internet 29. Alternatively, a remote site may also access the remote access gateway 11 directly through, for example, a dial-up telephone port, ADSL, or other types of private connection. Remote access gateway 11 may also be part of server 20 instead of standing alone, as well know in the art.

According to the principles of the present invention, executable application 19 (or multiple applications in another embodiment) resides on central server 20 on LAN 3 for gathering and processing data from multiple infusion pumps (and other devices and facilities) coupled to LAN 3 or hospital LAN 4. The acquired infusion pump data associated with a given patient is acquired from infusion pumps 8 and 6b (and other pumps not shown) on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. The server may be hosted, for example, by a computer system that is capable of running Microsoft NT operating system.

Figure 2:
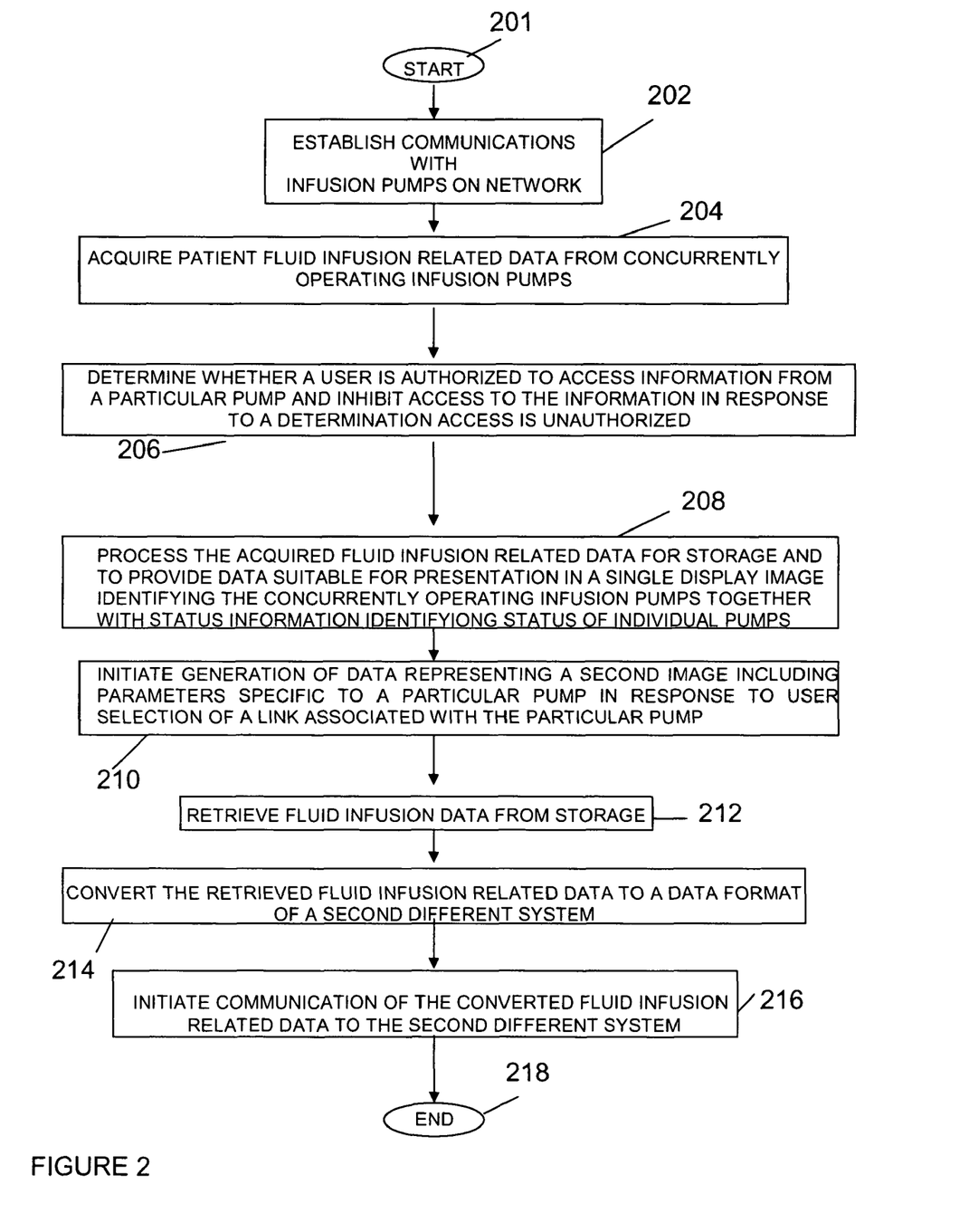
FIG. 2 represents a flowchart of a method for processing fluid infusion pump related data, according to the present invention.

FIG. 2 shows in flow chart form, functions that are performed by executable application 19. Application 19 establishes communication with concurrently operating infusion pumps (pumps 6b and 8) on the network in step 202 after the start at step 201. This is done, for example, by using IP protocol and the known IP device address for each pump on the network 1 (FIG. 1), in conjunction with any higher application-layer protocols, as well known in the art. Once communication is established between server 20 and the concurrently operating infusion pumps, application 19, in step 204, acquires fluid infusion related data from the pumps. The fluid infusion related data comprises parameters associated with fluid delivery, drip medication related parameters and other fluid related parameters.

Figure 3:
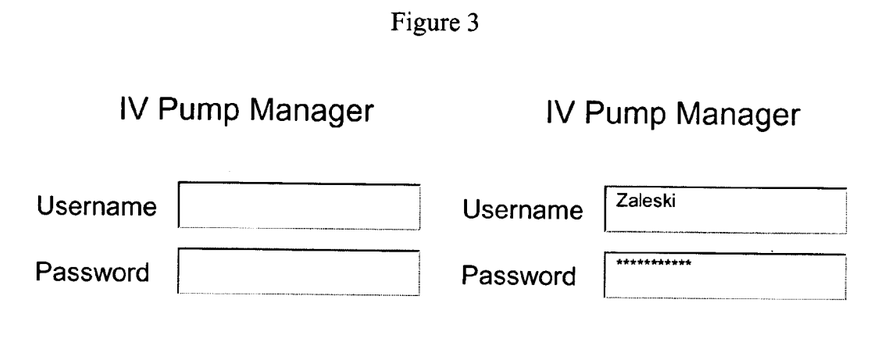
FIG. 3 shows logon data entry boxes in a user interface image, according to invention principles.

A user enters login information via the user interface image shown in FIG. 3 in order to access infusion pump information. Application 19 in step 206 determines whether a user is authorized to access information concerning an infusion pump and inhibits access to pump information (e.g., inhibits display of pump parameters) in response to a determination access is unauthorized based on received or missing login information. In response to a determination authorization is accessed, application 19 in step 208 processes the acquired fluid infusion related data for storage in a database and to provide data suitable for presentation in a single display image identifying the multiple concurrently operating infusion pumps together with status information identifying status of individual pumps.

Figure 4:
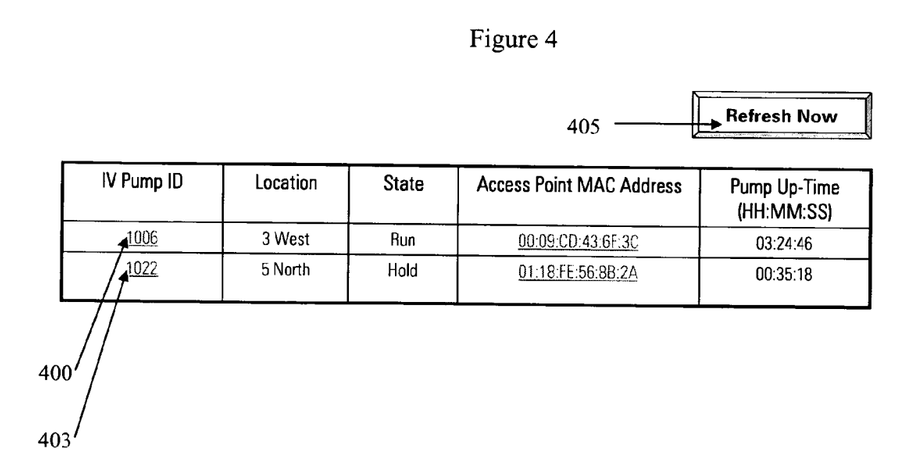
FIGS. 4 and 5 shows user interface display image windows showing data (and refreshed data respectively) related to infusion pumps for patients under the care of a particular healthcare provider, according to the present invention.
Figure 5:
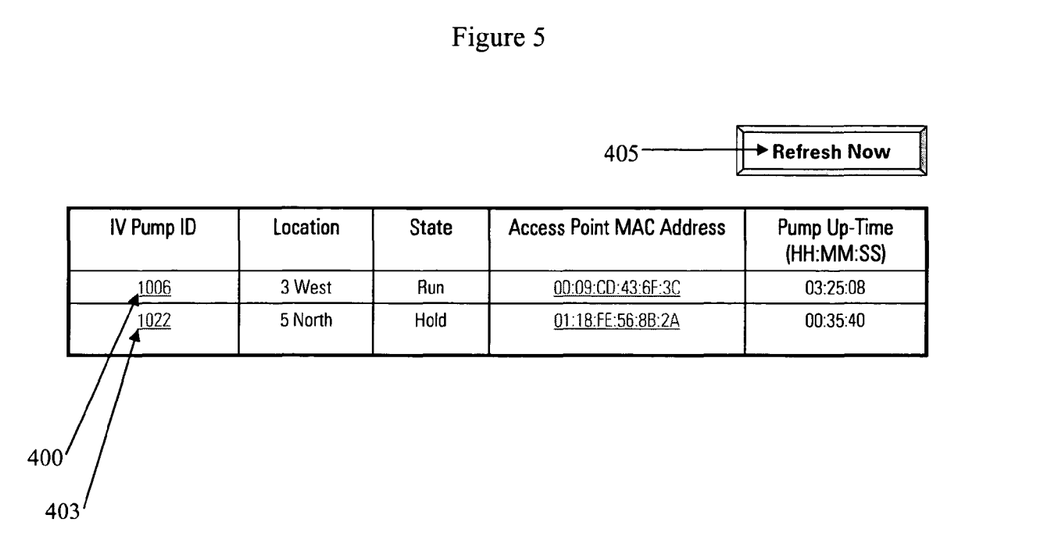

FIGS. 4 and 5 shows user interface display image windows generated in step 208 showing data (and refreshed data respectively) related to infusion pumps for patients under the care of a particular healthcare provider. Specifically, the image window of FIG. 4 shows acquired fluid infusion related data associated with two different pumps in rows 400 and 403 respectively. Specifically, FIG. 4 (and FIG. 5) shows the pumps authorized by, or for patients, under the care of a particular physician or nurse, for example. In other embodiments, FIG. 4 may show pumps used by a particular patient, or in a particular care unit or particular hospital department or all patients of a particular clinic or practice group, for example. The pump data includes a pump identifier, pump location, pump access address (e.g., pump IP or Ethernet MAC address), pump start time, pump flow rate, a fluid identifier in a pump, a pump status (e.g., operating, on hold or inactive) or fluid volume dispensed, for example. FIG. 5 shows the data of FIG. 4 updated as shown by the pump up-time values (03:25:08 and 00:35:40 in FIG. 5 versus 03:24:46 and 00:35:18 in FIG. 4) in response to user selection of refresh button 405. The display image of FIGS. 4 and 5 include user selectable links (links 1006 and 1022) associated with corresponding concurrently operating infusion pumps. The links represent hyperlinked objects that provide the capability to access data associated with corresponding particular pumps.

Figure 6:
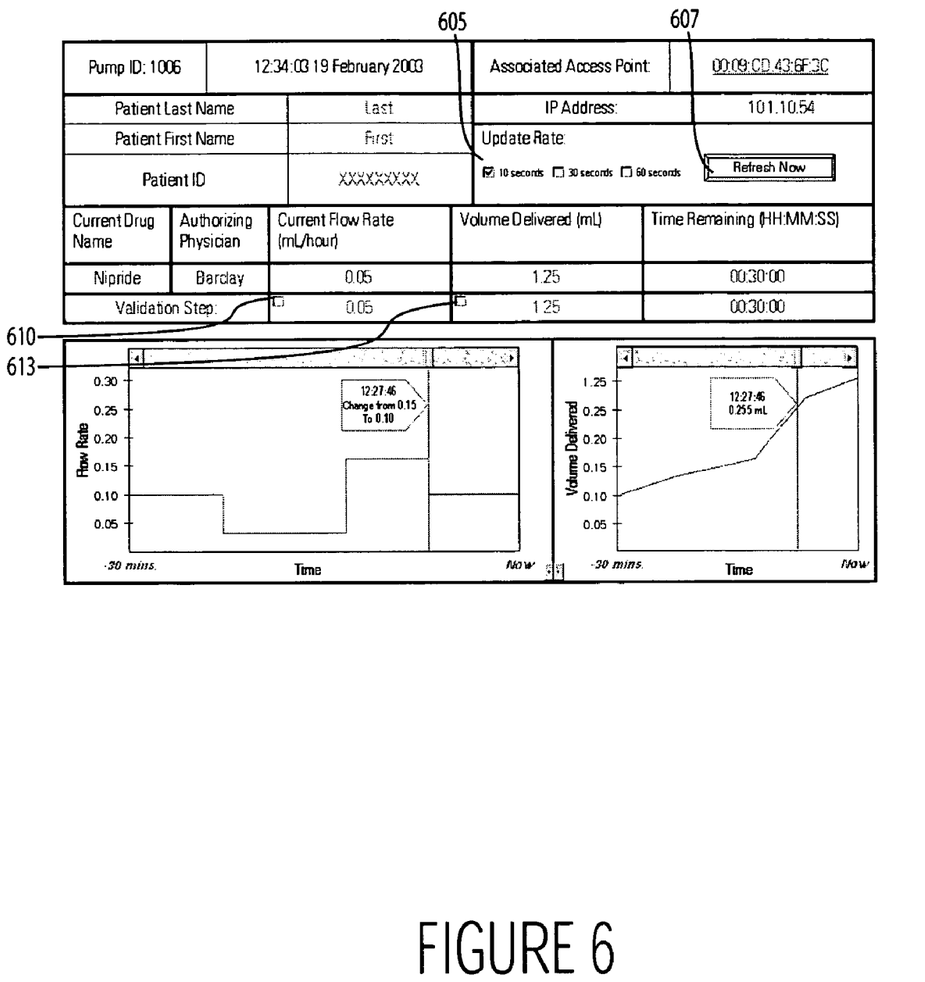
FIG. 6 shows a user interface display image window showing data related to a particular infusion pump that is displayed in response to a user pump link selection in FIG. 4, according to the present invention.

In step 210, application 19 initiates generation of data representing a second image including parameters specific to a particular pump in response to user selection of a link associated with a particular pump. FIG. 6 shows such a second image showing data related to a particular infusion pump that is displayed in response to user selection of link 1006 in FIG. 4. The infusion pump information of FIG. 6 includes at least one of, a current fluid flow rate, fluid volume delivered, a fluid identifier, a current time, a pump access point, an authorizing physician identifier, a fluid infusion time remaining indicator, a particular pump IP (or MAC or serial) address, a user selectable data refresh rate, a patient name, patient identifier, parameters specific to the particular pump and a user selectable item supporting user manual entry of a fluid infusion related value. Further, the user selectable item supporting user manual entry of a fluid infusion related value initiates generation of a third image enabling a user to, alter an existing infusion flow rate or fluid volume delivered value or to add a new infusion flow rate or fluid volume delivered value. Also, the FIG. 6 image further includes a graphical representation of fluid infusion flow rate and a graphical representation of infusion fluid volume delivered. The flow rate and volume delivered graphical representations cover a 30-minute (or other user selectable) duration and are shown together with a scroll bar that permits a user to move a cursor line across the graphical representation to note the exact time of a specific change associated with that parameter. The width of the graph plot windows may be changed using a drag bar located between the windows.

A user selects an automatic image data update rate via checkboxes in section 605 (here shown as 10 seconds, 30 seconds, or 60 seconds) of FIG. 6, or selects refresh button 607 to see the latest results in the FIG. 6 image. The FIG. 6 image further includes drug history, flow rate, and volume delivered to the patient, together with the time remaining (determined based on medication administration data input entered at the time the patient was placed on the infusion drip). A user is able to validate results (i.e., override a received result with a result deemed more accurate). For this purpose a user selects check box 610 or check box 613 contained within the "Current Flow Rate" and "Volume Delivered" fields respectively. In response to the check box selection, a menu is generated that gives a user the option of entering a value manually. A data field including a checked box becomes highlighted as bold and a user is permitted to change the result. The results are automatically sent via a Health Level 7 (HL7) protocol compatible result transaction to an outbound Internet Protocol (IP) port and server address e.g., of server 20 (FIG. 1). The results are stored in database 25 for use by a medication administration system or other clinical information system and for inclusion within an electronic patient record.

In step 212, application 19 retrieves fluid infusion related data from a database and in step 214 converts the retrieved fluid infusion related data to a data format of a second different system. The second different system comprises, a repository of electronic patient medical records, a pharmacy information system for use in re-stocking medications, a medication order information system for use in monitoring use of particular fluid medications or a patient management information system for use in monitoring patient usage of fluid medications, for example. In step 216 application 19 initiates communication of the converted fluid infusion related data to the second different system in response to user command and further processes the data to be suitable for presentation in a single display image. The process of FIG. 2 terminates at step 218.

Figure 7:
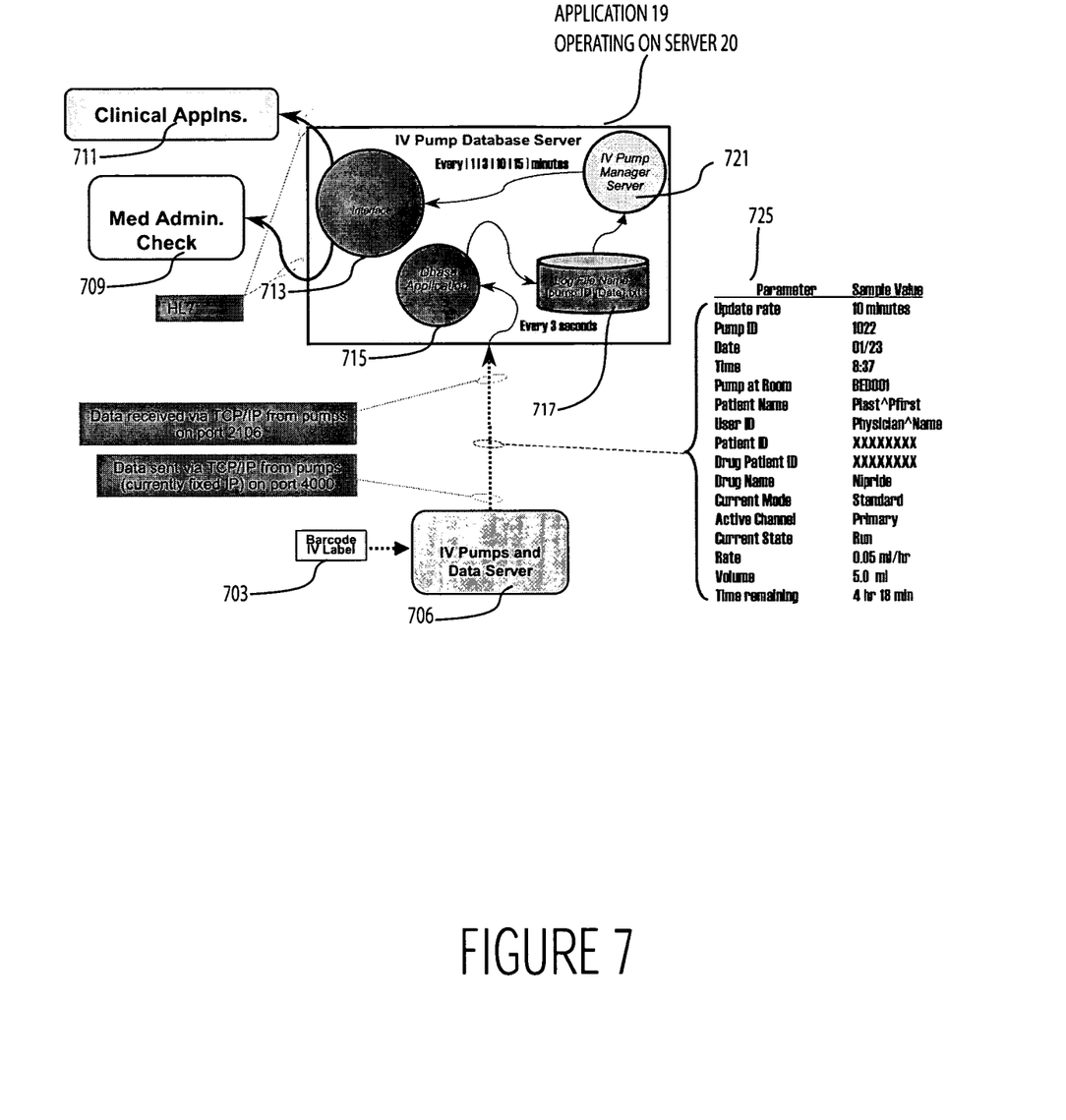
FIG. 7 shows a functional system for processing fluid infusion related data, according to the present invention.

FIG. 7 shows a functional system for processing fluid infusion related data acquired from infusion pump 706 by application 19 operating on server 20 using IP communication. The data, including parameters 725 and bar code label identifier 703, may be continuously, periodically or non-periodically acquired and correlated with a given patient for storage in relational data base 25 (FIG. 1) within server 20. Data base 25 may be of the type used for storing relational data such as a Microsoft SQL server. In addition, application 19 may obtain other medical data as well as patient parameter data and patient data comprising medical laboratory results that are first entered and stored, for example, in laboratory information system 17 of FIG. 1. Within application 19, database application 715 collates the acquired infusion pump data by pump identifier and acquisition time and date for storage in a file 717. Pump manager application 721 (within application 19) monitors stored infusion pump data in file 717 and processes and communicates infusion pump data (such as current pump state, volume delivered, flow rate) using interface application 713 to clinical applications 711 and a medication administration monitoring application 709 using Health Level 7 (HL7) protocol, for example. The data is accessible in substantially real time by authorized personnel via web browser 27 executing on a Microsoft Windows compatible PC 26, for example, within a hospital, or remotely via a LAN (Local Area Network) network.

A Web compatible viewer application (operating on PC 26 or on server 20) enables display of data related to multiple infusion pumps operating concurrently on a network in the form of HTML compatible web pages, for example. The viewer application enables a user to manage medication administration to patient and provides a graphical plotting function supporting a continually updated (or user initiated) display of infusion pump data to the user. The system further enables a user to view infusion pump data for multiple patients concurrently in a composite user interface image and is scalable to enable monitoring of infusion pump data for any number of patients within an enterprise.

Figure 8:
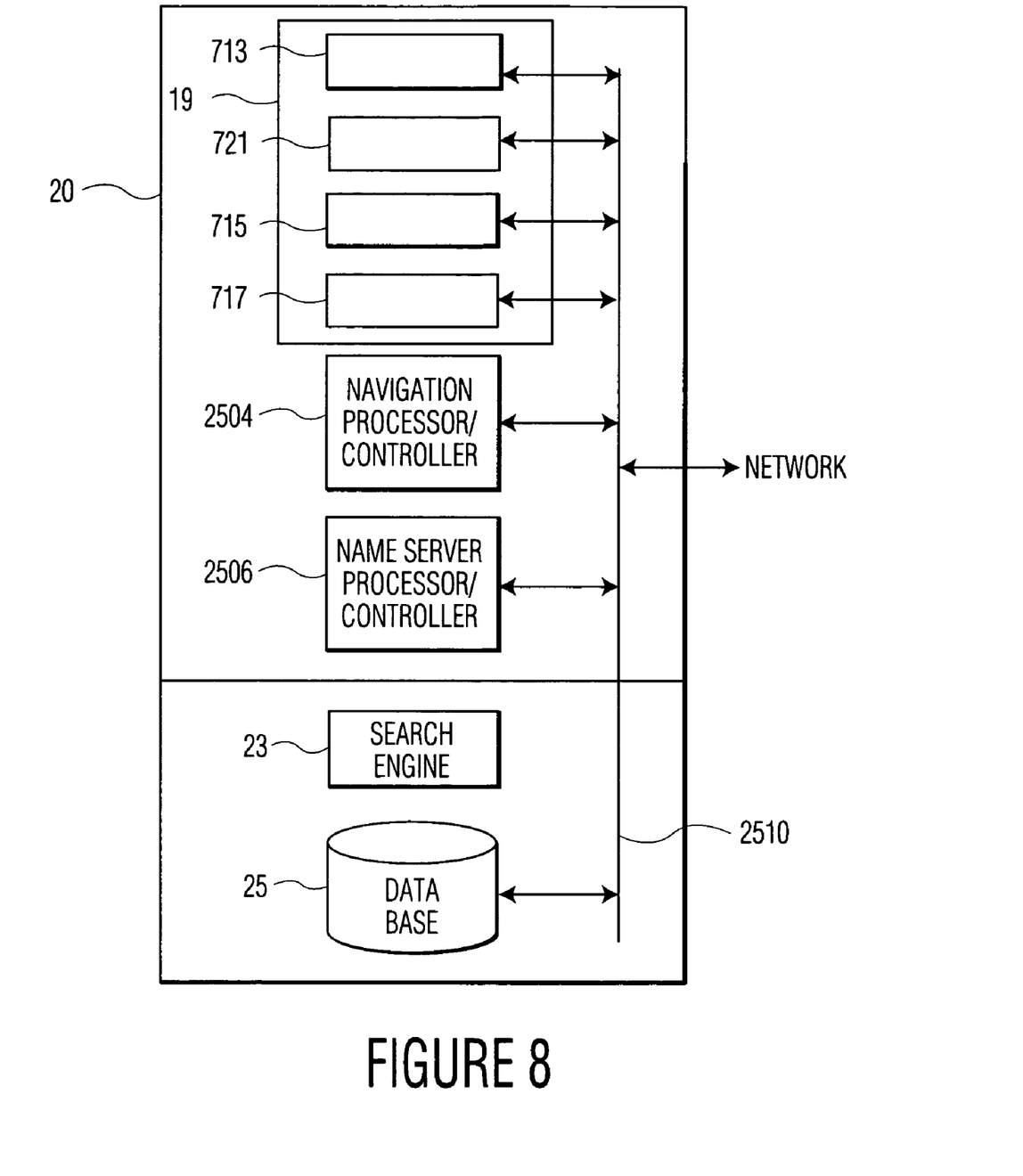
FIG. 8 is a block diagram of a server having functionality in accordance with the present invention.

FIG. 8 shows a block diagram of an exemplary embodiment of server 20 (FIG. 1) including functions in accordance with the present invention for processing and displaying infusion pump data and other medical data and storing the processed data in database 25 (FIG. 1). Application 19 includes database application 715, storage file 717, pump manager application 721 and interface application 713 as previously discussed for processing patient infusion pump parameters for storage in data base 25. Navigation collation processor 2504 operates in conjunction with web browser 27 on PC 26 and display generator software to collate and prioritize parameters for display to a user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The user interface display images, systems and processes presented in FIGS. 1-8 are not exclusive. Other user interface and processing systems may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A user interface and infusion pump management system and associated functions according to the invention may be used in other applications to support user viewing of substantially real-time device generated data.

What is claimed is:

1. An information system supporting a plurality of network connected infusion pumps, comprising:
   an acquisition processor for acquiring fluid infusion related data from a plurality of concurrently operating infusion pumps providing fluid infusion to a corresponding plurality of different patients in different locations;
   a data processor for processing said acquired fluid infusion related data to provide data suitable for presentation in a single display image identifying said plurality of concurrently operating infusion pumps together with status information identifying status of individual pumps of said plurality of concurrently operating infusion pumps, said display image includes a plurality of user selectable elements associated with said corresponding plurality of concurrently operating infusion pumps; and a display processor for initiating generation of data representing said single display image and a second image including parameters specific to a particular pump in response to user selection of a displayed element associated with said particular pump.

2. An information system according to claim 1, wherein said acquisition processor acquires said fluid infusion related data via a network and said acquired fluid infusion related data provides data associated with individual pumps including at least one of, (a) pump location, (b) pump access address, (c) pump start time, (d) pump flow rate, (e) a fluid identifier in a pump and (f) fluid volume dispensed.

3. An information system according to claim 2, wherein said plurality of concurrently operating infusion pumps are connected to an Internet Protocol (IP) compatible network and said pump access address is an IP address.

4. An information system according to claim 1, wherein said second image includes data identifying at least one of, (a) pump location and (b) an associated patient.

5. An information system according to claim 1, wherein said second image includes at least one of, (a) a current fluid flow rate, (b) fluid volume delivered, (c) a fluid identifier, (d) an authorizing physician identifier, (e) a fluid infusion time remaining indicator, (f) a particular pump IP address, (g) a current time, (h) a user selectable data refresh rate, (i) parameters specific to said particular pump and (j) a user selectable item supporting user manual entry of a fluid infusion related value.

6. An information system according to claim 5, wherein said second image includes at least one of, (a) a graphical representation of fluid infusion flow rate and (b) a graphical representation of infusion fluid volume delivered.

7. An information system according to claim 5, wherein said user selectable item supporting user manual entry of a fluid infusion related value initiates generation of a third image enabling at least one of, (a) a user to alter an existing infusion flow rate or fluid volume delivered value and (b) a user to add a new infusion flow rate or fluid volume delivered value.

8. An information system according to claim 1, including an authentication processor for determining a user is authorized to access information concerning an infusion pump and said data processor inhibits presentation of said second image including parameters specific to said particular pump in response to a determination access is unauthorized.

9. An information system according to claim 1, wherein said second image includes data identifies pump location and including an authentication processor for determining a user is authorized to access information concerning an infusion pump and said data processor inhibits access to pump information in response to a determination access is unauthorized.

10. An information system according to claim 1, wherein said data processor processes said acquired fluid infusion related data to provide data to at least one of, (a) a repository of electronic patient medical records for storage in a corresponding plurality of electronic patient medical records in said repository, (b) a pharmacy information system for use in re-stocking medications, (c) a medication order information system for use in monitoring use of particular fluid medications and (d) a patient management information system for use in monitoring patient usage of fluid medications.

11. An information system according to claim 1, wherein said acquisition processor acquires said fluid infusion related data via a network supporting communicatiion with said plurality of concurrently operating infusion pumps providing fluid infusion to a corresponding plurality of different patients in different locations.

12. A system supporting a plurality of network connected infusion pumps, comprising:

an acquisition processor for receiving fluid infusion related data from a plurality of concurrently operating infusion pumps providing fluid infusion to a corresponding plurality of different patients in different locations, said received data identifying said plurality of concurrently operating infusion pumps together with status information identifying status of individual pumps of said plurality of concurrently operating infusion pumps;

a data processor for processing said received fluid infusion related data to be suitable for storage in a database; and a conversion processor for retrieving fluid infusion related data from said database and for converting said retrieved fluid infusion related data to a data format of a second different system.

13. A system according to claim 12, wherein said conversion processor, converts said retrieved fluid infusion related data to a data format of a second different system comprising at least one of, (a) a repository of electronic patient medical records for storage in a corresponding plurality of electronic patient medical records in said repository, (b) a pharmacy information system for use in re-stocking medications, (c) a medication order information system for use in monitoring use of particular fluid medications and (d) a patient management information system for use in monitoring patient usage of fluid medications and initiates communication of said converted fluid infusion related data to said second different system in response to user command.

14. A system according to claim 12, wherein said conversion processor converts said retrieved fluid infusion related data to a data format suitable for presentation in a single display image.

15. An information system according to claim 12, wherein said acquisition processor receives fluid infusion related data from said plurality of concurrently operating infusion pumps using Internet Protocol (IP) compatible communication.

16. An information system according to claim 1 wherein said single display image shows said plurality of concurrently operating infusion pumps authorized by, or for patients, under the care of at least one of a physician, nurse, care unit, hospital department, clinic or practice group.

* * * * *